United States Patent [19]
Loeser

[11] 3,942,528
[45] Mar. 9, 1976

[54] NON-KINKING INTRAVENOUS TUBE LOOP DEVICE

[76] Inventor: Edward A. Loeser, 8646 Oak Valley Drive, Sandy, Utah 84070

[22] Filed: July 18, 1974

[21] Appl. No.: 489,478

[52] U.S. Cl........ 128/214 R; 128/133; 128/DIG. 26
[51] Int. Cl.².......................................... A61M 5/00
[58] Field of Search............ 128/133, 214 R, 214.2, 128/221, 348, 215, DIG. 26

[56] References Cited
UNITED STATES PATENTS

| | | | |
|---|---|---|---|
| 3,324,853 | 6/1967 | Czorny et al. | 128/214.4 |
| 3,511,232 | 5/1970 | Converse | 128/133 |
| 3,630,195 | 12/1971 | Santomieri | 128/133 |
| 3,826,257 | 7/1974 | Buselmeier | 128/214 R |
| 3,870,043 | 3/1975 | Dunn | 128/214 R |

FOREIGN PATENTS OR APPLICATIONS

| | | | |
|---|---|---|---|
| 723,464 | 1/1932 | France | 128/133 |

Primary Examiner—Dalton L. Truluck
Attorney, Agent, or Firm—Trask & Britt

[57] ABSTRACT

A base member having a side surface and a bottom surface is provided. First and second ports are formed in the side surface which are interconnected by a channel in the base member. An intravenous system tube may be passed through the first port and channel and out the second port to provide for reversal of fluid flow in the tube with respect to the direction of fluid flow in the tube at the first port. The channel is formed to preclude kinking of the tube. Alternately, intravenous fluid system tubing may be adapted to the first and second ports. The tubing connects to an intravenous fluid supply and to a catheter apparatus. Means may be adapted to a top surface of the base member to permit the injection of medications into the fluid passing through the channel or the tubing in the channel.

13 Claims, 7 Drawing Figures

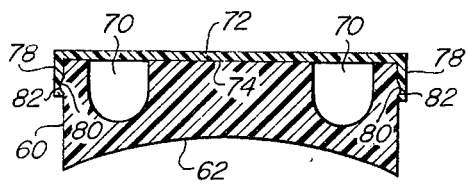
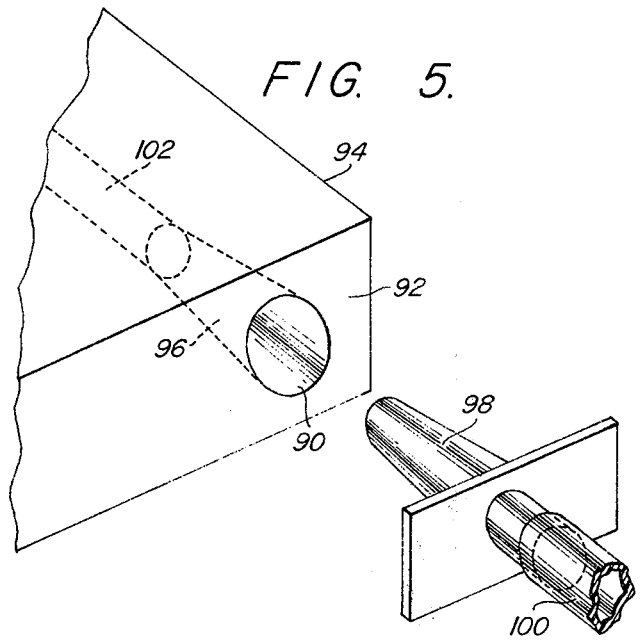
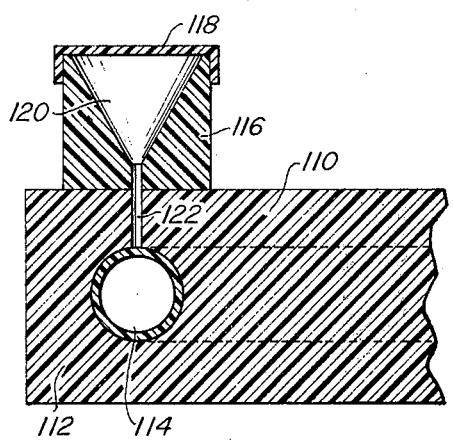

NON-KINKING INTRAVENOUS TUBE LOOP DEVICE

BACKGROUND OF THE INVENTION

1. Field

This invention relates to intravenous therapy systems. More particularly, this invention provides a device to effectively form a loop in intravenous supply tubing to change the direction of flow of the intravenous fluids while precluding inadvertant restriction or interruption of the fluid flow.

2. State of the Art

Intravenous (IV) therapy systems are well known. In general, they include a fluid supply and catheter apparatus with interconnecting tubing. The catheter apparatus are frequently of the type which is comprised of a stylet in a cannula attached to a hub. The stylet and cannula are inserted into a patient's vein in the forearm area with the stylet and cannula moving into the vein in a direction from the wrist toward the elbow. After the stylet is removed, the IV system tubing is connected to the hub. If the tubing is led directly away from the patient's forearm to the IV fluid supply, the movement of the arm by the patient is limited. Accidental movement often results in a dislodging of the catheter apparatus. The IV therapy (i.e., catheter apparatus) must then be moved to a new IV site. Increased patient discomfort along with potential trauma results. See: D. Maki, et al., *Infection Control in Intravenous Therapy*, Annals of Internal Medicine 79:867 to 887 (1973). Accordingly, the practice has developed to form a loop in the IV tubing below the catheter apparatus and tape the tubing along the forearm and upper arm to the vicinity of the shoulder. At that point the tubing is led away to the IV fluid supply. Thus, the patient is allowed some arm movement without hazarding the IV therapy.

Many times the loop formed in the tubing in the forearm area kinks. That is, the tube, being flexible, is bent or flexed to such a degree that the inner cross section of the tube is reduced. Such a kink abnormally restricts and reduces the prescribed flow of IV fluid. A kink may also completely stop IV fluid flow. A device such as that disclosed in U.S. Pat. No. 3,630,195 (Santiomieri) seeks to hold the IV tube and loop in place. However, it does not effectively preclude kinking in the tube loop. Further, the loop formed when using the device is of such diameter that the loop frequently snags on bedding and the like. Also, it is too cumbersome to use on small patients such as an infant.

The problem of kinking is even more severe in a hospital operating room environment. IV therapy is frequently prescribed before and during surgical operations. The IV site (e.g., the forearm) is generally covered with antiseptic coverings during the surgery. A kink is thus difficult to detect and if detected is difficult or hazardous to correct. The operating surgeon must often cease activity to allow attending personnel to correct the malfunction. That in itself is medically hazardous. Moreover, movement of the coverings increases the potential for infection subsequent to the surgery. Accordingly, it is important that kinking of the IV tubing be eliminated.

SUMMARY OF THE INVENTION

A non-kinking intravenous tube loop device includes a base member having a side surface and a bottom surface for positioning adjacent the skin of a patient. A first and second port is formed in the side surface. A channel is formed in the base member to interconnect the first and second ports. Intravenous tubing is adapted to the first and second ports. Intravenous fluids passing through the second port are changed in direction with respect to the fluids passing through the first port.

In one form of the invention, intravenous tubing is passed through the first port and channel and out the second port. The first end of the IV tubing is then connected to an IV fluid supply, and the second end is connected to a catheter apparatus. The channel in the base member is formed and the first and second ports positioned so that the IV tubing and the fluid in the channel reverse directions with respect to the direction of IV tubing and fluid at the first port and so that kinks in the tubing are precluded.

In another form of the invention, first and second connector means are adapted to the first and second ports respectively. The first connector is connected to an IV fluid supply by IV tubing. The second connector is connected to a catheter apparatus. The IV fluid passes through the first port and interconnecting channel and out the second port. The ports and channel are formed such that the direction of flow of the fluid out of the second port is opposite to the direction of fluid flow into the first port.

In yet another form of the invention, means are adapted to the top surface of the base member to permit the injection of medicines into the IV fluid. Also, the bottom surface of the base member may be concave to facilitate the positioning of the loop device on the arm of a patient.

In a further embodiment, the base member may be fabricated with the top surface comprised of a lid. Upon removal of the top surface (lid), the channel and ports are exposed to permit the installation of tubing which may have adapters and/or connectors secured at its opposite ends. Securing means is provided to secure the lid to the base member.

BRIEF DESCRIPTION OF THE DRAWINGS

In the drawings which illustrate the best mode presently contemplated for carrying out the invention.

FIG. 4 is a cross sectional view of the device of FIG. 3 at the section lines 4—4;

FIG. 5 is a partial perspective view of an alternate embodiment of a non-kinking intravenous tube loop device of the invention;

FIG. 6 is a partial sectional view of a non-kinking intravenous tube loop device of the invention with means for injecting medications adapted thereto; and FIG. 7 is a perspective cut-a-way view of another embodiment of a non-kinking intravenous tube loop device of the invention.

DESCRIPTION OF THE ILLUSTRATED EMBODIMENT

Figure 1:
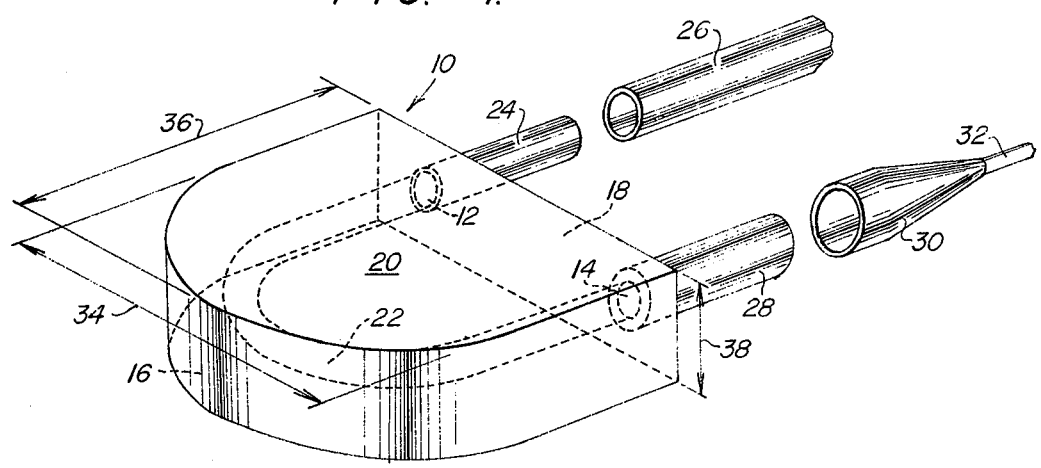
FIG. 1 is a perspective of one embodiment of a non-kinking intravenous tube loop device of the invention.

FIG. 1 depicts a non-kinking intravenous tube device of the present invention. It includes a base member 10, a first port 12 and a second port 14. The base member 10 has a bottom side 16 which may be concave in section to facilitate positioning on the arm of a patient. The ports 12, 14 are formed in a side surface 18 of the base member 10. As here illustrated, the side surface 18 is a substantially flat surface generally normal to the bottom 16 and top 20 surfaces of the base member 10. A channel 22 is formed in the base member 10 interconnecting the first port 12 and the second port 14. The channel is preferably U shaped in projection. As here illustrated, the first connector means is a cylindrical extension 24 adapted to the first port 12. Intravenous tubing 26 is removably connectable to the extension 24 by sliding it on and off of the extension 24. The tubing 26 connects to an intravenous fluid supply (not illustrated) in a manner well known to those skilled in the art.

Second connector means is adapted to the second port 14. The second connector means is a cylindrical extension 28 secured to the second port 14. The extension 28 adapted to be removably secured to the hub 30 of the catheter apparatus.

In operation IV fluid from the intravenous fluid supply passes through the IV tubing 26, through the first port 12 and the channel 22 and out through second port 14 and into the hub 30 and the patient's vein through cannula 32 which has been positioned therein. As illustrated, the direction of fluid flow out of the base member is reversed with respect to the direction of flow into the base member through first port 12.

The base member 10 is secured to a patient by securing means which may be surgical tape placed on the top surface 20 and extending onto the skin of a patient in a manner well known to those in the art. The base member 10 and cylindrical extensions 24, 28 are preferably fabricated of a plastic-like material, although any material which is sterilizable and otherwise medically suitable may be used. The base member 10 may be dimensioned to create several sizes to be adaptable to different sized patients (e.g., infant to large adult). Preferably, the base member 10 is from about ¾ inches to 1½ inches wide 34, about ¾ inches to 1½ inches long 36 and about ¼ inch to ½ inch high 38. Such dimensions facilitate use of the invention with patients of virtually all sizes.

Figure 2:
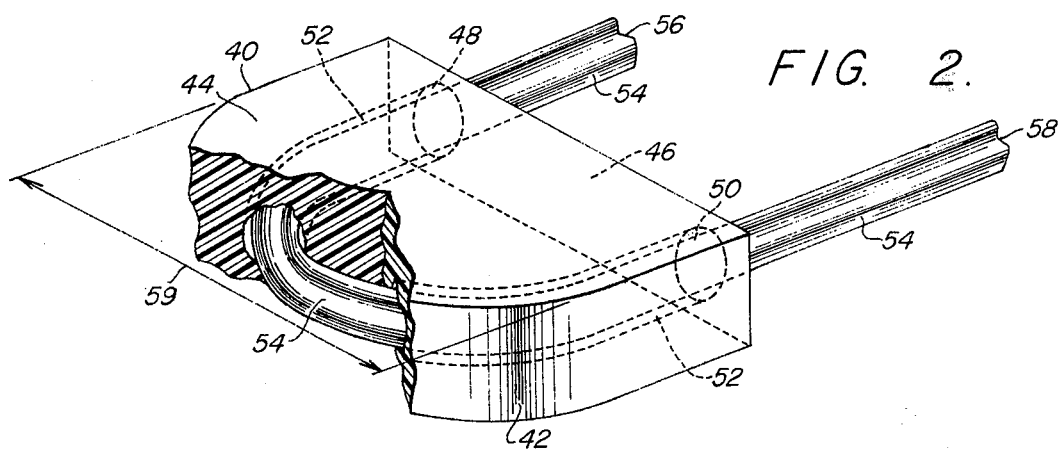
FIG. 2 is a perspective cut-a-way view of another embodiment of a non-kinking intravenous tube loop device of the invention.

Another embodiment of the invention is illustrated in FIG. 2. The base member 40 includes a bottom surface 42, a top surface 44 and a side surface 46. First 48 and second 50 ports are interconnected by a channel 52. As depicted, the channel 52 is preferably circular in cross section and sized in diameter slightly larger than the diameter of the IV tubing 54. The channel 52 is also U shaped to preclude the formation of kinks in the tubing 54. The tubing 54 may thus be slideably pushed or threaded through the first port 48 and channel 52 and out the second port 50. The first end 56 of the IV tubing 54 is connectable to an IV fluid supply, and the second end 58 is connectable to a catheter apparatus.

The device of FIG. 2 is manufactured of a plastic-like material similar to the device of FIG. 1. In dimension, however, it is slightly wider, being from about 1 inch to 1¾ inches wide 59. The additional width 59 is provided to preclude kinking in the tube 54 in the base member 40.

Figure 3:
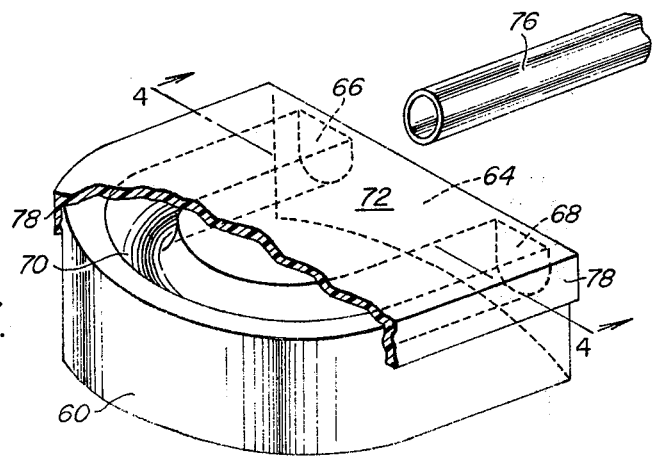
FIG. 3 is a perspective cut-a-way view of another embodiment of a non-kinking intravenous tube loop device of the invention.

FIGS. 3 and 4 illustrate another embodiment of the present invention. The base member 60 has a bottom surface 62 and a side surface 64. First 66 and second 68 ports are formed in the side surface 64. A channel 70 interconnects the ports 66, 68. The channel 70 is preferably U shaped in cross section and projection. A removable top surface or lid 72 is positioned on top of the base member 60. The channel 70 is formed to extend from the inner top surface 74 of the base member 60 downward and is shaped and dimensioned to receive IV tubing 76. With the lid 72 removed, the IV tubing 76 is positioned in the channel 70 with first and second ends extending from the first 66 and second 68 ports for connection to an IV fluid supply and a catheter apparatus respectively. The lid 72 is then positioned over the base member to secure the IV tubing 76 in place. The lid 72 is secured to the base member by securing means which as here illustrated is a flange 78 and ridge 80 arrangement. The flange 78 has a groove 82 and is capable of flexing outwardly. As the lid 72 is pressed onto the base member 60, the flange 78 slides over the ridge 80 and coacts with the groove 82 in a well known manner.

The device illustrated in FIGS. 3 and 4 is constructed of plastic-like material similar to the devices shown in FIGS. 1 and 2. Also, the device of FIGS. 3 and 4 is dimensioned similar to the device of FIG. 1.

The bottom surface 62 of base member 60 in FIG. 4 is concave in axial cross section. The same feature is applicable to the other embodiments herein illustrated. With the surface formed as illustrated, securing the loop device to the arm, leg or neck of a patient is facilitated.

FIG. 5 illustrates an alternate connector means for use with embodiments similar to that illustrated in FIG. 1. An enlarged port 90 is formed in the side surface 92 of the base member 94. The port 90 connects to a tapered cavity 96 which is sized and shaped to receive a conventional IV tubing male connector 98. Tubing 100 is connected to the connector 98 and to an IV fluid supply or catheter apparatus. The cavity 96 connects to the channel 102 which is interconnected to the other port (not shown) in a manner as hereinbefore described.

FIG. 6 illustrates one form of means which may be adapted to the top surface 110 of a base member 112 to permit the insertion of medications into the IV fluids passing through the channel 114 or the tube (not illustrated) in the channel. The means depicted includes a cylindrical tower 116 fixedly secured to the top surface 110, a penetrable flexible cap 118, and a cavity 120 in the tower 116 in communication with the channel 114 through an aperture 112 formed in the base member 112. The needle of a conventional syringe (not shown) may be inserted through the cap 118, cavity 120 and aperture 122 into the channel 114. Medications in the syringe may thus be directly injected into the IV fluids and in turn into the patient. Use of means for injecting medications having a tower or equivalent structure is preferred. In an operating room environment, the antiseptic coverings arranged about the patient may be arranged to allow the tower structure to extend outside the coverings to facilitate the administration of medications therethrough during surgery.

FIG. 7 depicts yet another embodiment of the present invention. The base member 130 has a bottom side 132 and a side surface 134 with first 136 and second 138 ports formed therein. The ports 136, 138 are interconnected by a channel 140 formed in the base member 130. IV tubing 142 is adapted to both ports 136, 138, although as here shown it is adapted only to the second port 138. The tubing 142 is connectable to a catheter apparatus or an IV fluid supply as herinbefore described. The tubing 142 is adapted to the ports 136, 138 by glue or other means well known in the art. The tubing 142 may extend past the port 136, 138 into the block 130 and the channel 140 as necessary to effect adaptation.

The device in FIG. 7 is particularly useful for use with an IV tubing system. That is, the IV tubing arrangement used to connect an IV bottle (IV fluid supply) to a catheter often is manufactured and sold as a system which includes other features not here relevant. The device depicted in FIG. 7 is dimensioned to facilitate incorporation into such tubing systems at manufacture. For example, the block illustrated may be about ½ inch wide 144, ⅜ inch high 146, and ⅝ inch long 150. These dimensions facilitate adaptation with IV tubing arrangements where the tubing is about 5/16 inch in outside diameter. With such dimensions, it should be noted that the channel 140 need not be formed as a distinct U shaped channel as illustrated. The channel 140 may simply be a cavity formed in the base member 130 with the ports 136, 138 in communication with the cavity.

It should be noted that use of the non-kinking device of the invention herein disclosed increases the reliability of intravenous therapy. The practice heretofore has often been to form and tape a loop of IV tubing to the skin of the patient. Taping in itself tends to be excessive which in turn causes some patient discomfort. With such a loop, the elastic characteristics of the flexed or bent IV tubing produces a force (to straighten out) which tends to dislodge the catheter apparatus. If a catheter apparatus is dislodged, IV therapy must be shifted to a new site on the patient, increasing the hazards from infection and other trauma. The device of the instant invention may be installed to apply force to hold the catheter apparatus in place. For example, in FIG. 1, the base member 10 may be positioned to force and hold the catheter apparatus (hub 30 and cannula 32) in place. Thus, use of the device herein disclosed may tend to reduce IV therapy site consumption. Furthermore, with the catheter apparatus held securely in place as above described, it need not be extensively secured with tape as is the practice. Taping may be limited to a small piece of tape placed directly over the IV site to guard against infection and dislodgment. Such a small piece of tape will facilitate frequent inspection of the IV site by attending personnel.

It should also be noted that the fluid flow direction change effected by use of the device herein may be less than 180°. That is, the degree of flow direction change may be varied. As illustrated the flow direction change is about 180° plus or minus 5°. It is within contemplation that flow direction changes as small as 10° may be effected in the manner illustrated. However, as presently envisioned, it appears to be particularly practical to employ the disclosed invention for flow direction changes of from about 90° to about 180°.

It is to be understood that the embodiments of the invention herein described are merely illustrative of the application of the principles of the invention. Reference herein to details of the illustrated embodiments is not intended to limit the scope of the claims which themselves recite those features regarded as essential to the invention.

I claim:

1. An intravenous tube loop device comprising:

a. a base member having (1) a side surface and (2) a bottom surface for positioning adjacent the skin of a patient;
    b. a first port formed in said side surface;
    c. first connector means to removably connect intravenous fluid supply tubing to said first port;
    d. a second port formed in said side surface;
    e. second connector means to removably connect said second port to an intravenous catheter apparatus; and
    f. channel means to interconnect said first port and said second port which permits the flow of fluids therebetween and which changes the direction of the flow of said fluids with respect to the direction of the flow of said fluids at said first port.

2. The intravenous tube loop device of claim 1 wherein the direction of said fluid flow at said second port is substantially reversed with respect to the direction of flow at said first port.

3. The intravenous tube loop device of claim 1 wherein said base member has a top surface with means adapted thereto in communication with said channel to permit injection of medications into said fluids in said channel.

4. The intravenous tube loop device of claim 1 wherein said channel is circular in cross section and U shaped in projection, and wherein said bottom surface is concave in axial cross section to facilitate positioning on the arm of a patient.

5. The tube loop device of claim 1 wherein said first connector means is comprised of coacting male and female connectors alternately and selectively adapted to said base member in communication with said first port and to said intravenous tubing and said second connector means is comprised of coacting male and female connectors alternately and selectively adapted to said base member in communication with said second port and to said intravenous catheter apparatus.

6. The intravenous tube loop device of claim 1 wherein said first connector means is a cylindrical extension secured to said first port and adapted to removably receive intravenous tubing thereover, and wherein said second connector means is a cylindrical extension secured to said second port and adapted to removably connect to the hub of said intravenous catheter apparatus.

7. The intravenous tube loop device of claim 6 wherein said first connector means includes glue means to fixedly secure said intravenous fluid supply tubing to said first port, and wherein said second connector means is intravenous fluid tubing fixedly secured by glue means at its first end to said second port and removably adaptable to said catheter apparatus at its second end.

8. The intravenous tube loop device of claim 7 wherein said base member is constructed of plastic and sized to be about ½ inch wide, ⅜ inch high and ⅝ inch long.

9. The intravenous tube loop device of claim 1 wherein said first port, second port and channel are sized in cross section to permit said intravenous fluid supply tube to be passed through said first port and said channel and out said second port for said connection to said catheter apparatus.

10. The intravenous catheter apparatus of claim 9 wherein said channel is circular in cross section and U shaped in projection, and wherein said bottom surface is concave in axial cross section to facilitate positioning on the arm of a patient.

11. The intravenous tube loop device of claim 10, wherein said base member has a top surface constructed as a removable lid, so that when said lid is removed said first and second ports and said channel are exposed to permit placement of said tubing through said first and second ports and said channel.

12. In combination with an intravenous therapy system which includes (1) a supply of intravenous fluid, (2) a catheter apparatus for injecting said fluids into a blood vein of a patient, and (3) tubing interconnecting said supply of intravenous fluid and said catheter apparatus, a tube loop device comprising:
 a. a base member having (1) a side surface and (2) a bottom surface for positioning adjacent the skin of a patient;
 b. a first port formed in said side surface;
 c. first connector means to removably connect intravenous fluid supply tubing to said first port;
 d. a second port formed in said side surface;
 e. second connector means to removably connect said second port to an intravenous catheter apparatus; and
 f. channel means to interconnect said first port and said second port which permits the flow of fluids therebetween and which changes the direction of flow of said fluids with respect to the direction of the flow of said fluids at said first port.

13. The combination of claim 12 wherein said intravenous fluid supply tube is adapted to said first port by glue means, and wherein said intravenous catheter apparatus is adapted to said second port by means which include intravenous tubing adapted to said port by glue means at its first end and removably connected to said intravenous catheter apparatus at its second end.

* * * * *